United States Patent [19]

Seavitt

[11] 4,338,938
[45] Jul. 13, 1982

[54] WASHABLE DIAPER

[76] Inventor: Susan A. Seavitt, 975 Plymouth, SE., Grand Rapids, Mich. 49506

[21] Appl. No.: 151,353

[22] Filed: May 19, 1980

[51] Int. Cl.³ .................................... A61F 13/10
[52] U.S. Cl. .............................. 128/284; 128/287
[58] Field of Search ............................ 128/287, 284

[56] References Cited

U.S. PATENT DOCUMENTS

| 3,162,196 | 12/1964 | Salk | 128/287 |
| 3,719,189 | 3/1973 | Sherman | 128/287 |
| 4,050,462 | 9/1977 | Woon et al. | 128/287 |

FOREIGN PATENT DOCUMENTS 2335165  7/1977  France .............................. 128/287

Primary Examiner—Marion McCamish
Assistant Examiner—B. K. Johnson
Attorney, Agent, or Firm—Price, Henveld, Huizenga & Cooper

[57] ABSTRACT

A reuseable diaper is disclosed made of plural layers of material to provide a soft, absorbent inner face and an outer face having a soft fabric texture with an inner layer of moisture impervious material. The diaper incorporates elastic material to enable it to fit about an infant's body. The materials used for the diaper are suitable for repeated washing and reuse.

1 Claim, 3 Drawing Figures

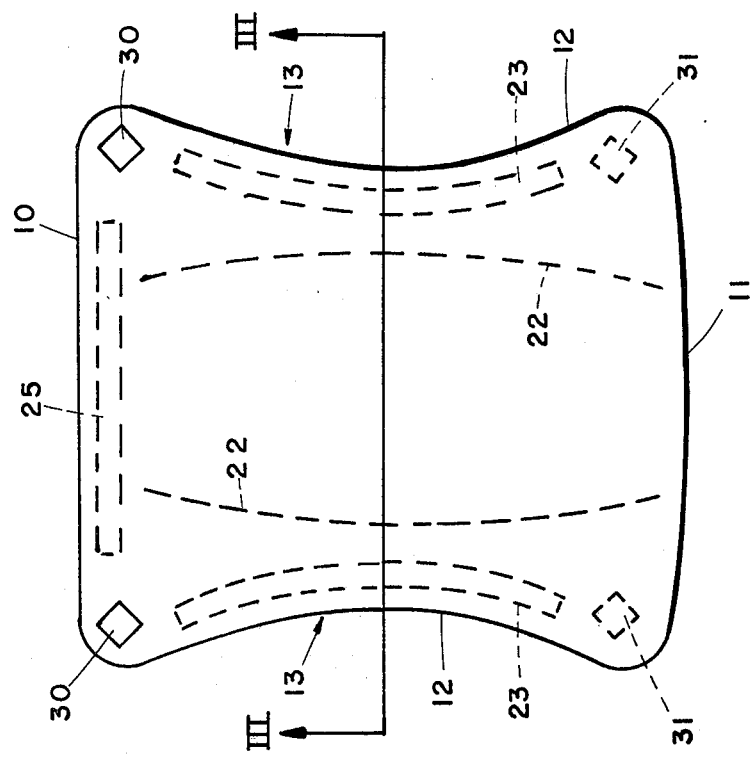
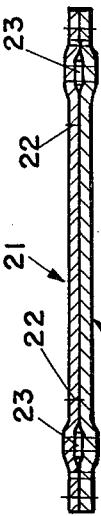
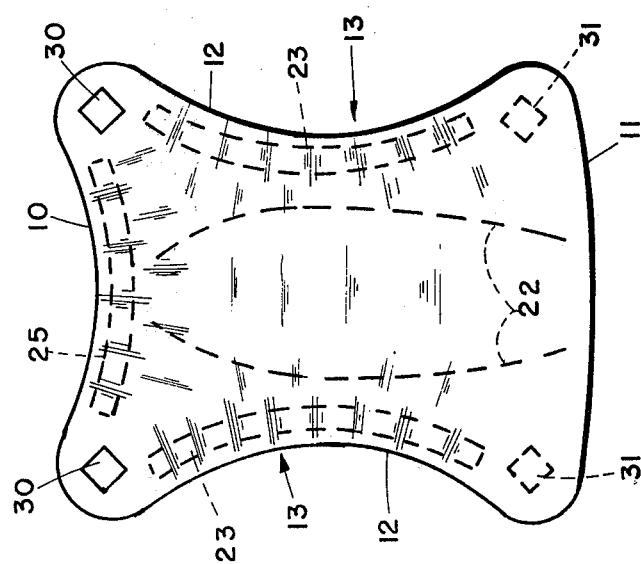

WASHABLE DIAPER

BACKGROUND OF THE INVENTION

This invention relates to infants' garments and particularly to a washable and reusable diaper. While washable and reuseable diapers have been known and used for many years, they have in recent years been largely displaced by single use, disposable diapers manufactured of paper material. Such diapers are of the so-called convenience type.

As the cost of materials has been steadily increasing, so has the cost of the so-called convenience or disposable diaper. Further, materials now available make it possible to develop a reusable diaper which will retain both its pliable softness and its ability to remain moisture impermeable over a long period of time despite repeated laundering. There has also been a growing recognition that the disposal of large quantities of materials such as disposable diapers can, in some areas, have an adverse affect upon the environment because of the excessive demands placed upon water resources and the quantities of digestion chemicals necessary to effect disposal. For persons living in areas not served by community sanitary disposal facilities, such disposable materials can and do cause serious malfunction of private sanitary facilities.

BRIEF DESCRIPTION OF THE INVENTION

The diaper of this invention is of the laminar or multilayer type, with one layer providing the absorbent, soft, skin contacting layer and a second layer which provides a moisture impermeable film or barrier against leakage. These layers are combined in a diaper of a somewhat dog-bone shape having a pair of curved sides which create a narrow, central waist with a pair of ends which extend or flair outwardly. One end and two opposed sides are provided with elastic materials so that the diaper may be stretched and reshaped to seat around the body of the infant, providing control against the escape of liquids while at the same time exerting only gentle pressure against the infant's body. The materials of the diaper are such that they will remain soft, pliable and absorbent throughout repeated washing cycles. The diaper, in its preferred form, is equipped with nonmetallic fasteners which will not rust nor deteriorate even though the diapers are repeatedly washed in hot enough water to assure adequate sterilization. The fasteners are a permanent part of the diaper, eliminating the necessity for the use of more conventional clips or safety pins.

BRIEF DESCRIPTION OF THE DRAWINGS

FIG. 1 is a flat-pattern view of the inside of the diaper when it is not stretched or tensioned and is laid on a flat surface;

FIG. 2 is a view similar to FIG. 1 but showing the diaper in stretched condition; and FIG. 3 is a sectional view taken along the plane III—III of FIG. 1.

DESCRIPTION OF THE PREFERRED EMBODIMENT

The diaper of this invention is illustrated in FIG. 1 in its nonstretched or relaxed condition. It will be seen from this view that the diaper has a first end 10 and opposite end 11 and a pair of sides 12. The sides 12 are so designed that each has a shape somewhat similar to a segment of a circle. These sides curve inwardly, thus producing a garment having its narrowest portion at the waist area 13 intermediate the ends of the diaper. When the diaper is stretched, as indicated in FIG. 2, while the waist area 13 is widened, it still remains the narrowest portion of the garment. One end 10 of the garment in its relaxed or unstretched state is inwardly curved similar to one of the sides 12. The other end 11 is slightly outwardly curved as indicated in FIGS. 1 and 2.

The garment consists of multiple layers or laminae of material. The outer layer 20 is formed by sheet material having a woven, preferably cotton, exterior surface and a latex, moisture impervious film on the interior surface. These two materials are bonded together in such a manner that the exterior has the finish and feel of a woven fabric, preferably cotton, while the interior has a continuous film of the latex material. Latex is important to this type of material because it can withstand repeated washing at temperatures adequate for effective sterilization without losing its flexibility and pliability and without loss of its moisture impervious characteristics. Such material is well known and is used in hospitals and similar institutions as a moisture barrier sheet on beds, operating tables and the like.

The inner lamina 21 consists of multiple layers. The individual layers are not illustrated in FIG. 3 for sake of clarity. These layers are of loosely woven cotton fabric, having weave that is stretchable. It is also characterized in that it is highly absorbent of moisture. The lamina 21 consists of plural layers, preferably three or more, of this material. These layers are tied together at spaced intervals by suitable stitching such as the stitching 22. This type of material is commercially available and has for some time been sold for use where high absorbency, softness and resistance to repeated washing without loss of pliability and softness is desired. Typically, it is used for diapers, polishing cloths and the like.

Adjacent each of the sides 12 a strip 23 of elastic material is sandwiched between the laminae 20 and 21 and secured to both the inner and outer lamina by suitable stitching 24. These are sewn to the inner and outer laminae while the elastic is stretched. Thus, when the elastic is released, it causes the fabric layers to contract and form pleats along the sides 12. The same construction is utilized at the end 10 with an elastic band 25 embedded between the layers of the garment.

It will be noted from FIGS. 1 and 2 that in the case of the elastic bands 23 along the side and the elastic band 25 at the end 10, the band terminates at a point substantially short of the ends of the sides 12 and in the case of the end 10, terminates well short of the sides. Thus, all four corners of the diaper have a substantial area or tab in which there is no elastic. Exterior of the elastic bands 23 and 25 and entirely encircling the diaper, the edges are stitched in a suitable manner such as by overcasting or zig-zag stitching to reinforce them providing a positive and durable attachment of the inner and outer laminae and also positively preventing any ravelling of the woven layers of the inner fabric 21. It will be noted that no elastic is provided along the end 11 of the diaper.

The diaper, after it has been placed on an infant, is secured by means of nonmetallic detachable means. For this purpose small patches of suitable, interengaging, plastic separable materials 30 at one end and 31 at the opposite end are provided. These are preferably of the interhooking, molded plastic type such as that sold under the trademark Velcro. The patches 30 at the end 10 are secured to the inner face of the diaper while the patches 31 at the end 11 are secured to the outer face of the diaper so that the patches will overlay each other when the diaper is wrapped about the infant.

It will be noted from FIG. 2 that when the diaper is stretched to its maximum size the sides 12 retain some of their inward curvature as indicated at 13 in FIG. 2 while the end 10, in effect, becomes straight. Since the end 11 does not have any of the elastic, its length remains constant. When the diaper is placed on an infant, the curved sides 12 wrap about the legs while the stretchable end 10 is wrapped about the back of the infant. This brings the fastener patches 31 and 30 into a position where they can be snapped together. The elastic material provides a clamping action which is gentle yet sufficient to assure positive contact between the edges of the garment and the torso and legs of the infant to trap moisture and prevent it from escaping. Because of the high absorbency of the inner layers 21, the moisture is retained against migration sideways or lengthwise of the diaper, thus further controlling leakage. Because of the elastic along the three edges of the diaper, the diaper is able to accommodate a reasonable degree of growth without binding the infant in a manner to cause either injury or discomfort. It also permits the diaper to stretch, providing freedom of movement without undue restriction. By using cotton, the diaper may be washed many times without loss of strength or softness and pliability and without developing a scratchy or irritating surface. The elimination of metallic fasteners disposes of any problem or discomfort arising from the presence of hard or lumpy materials which could cause discomfort or irritation. The use of an exterior material having an inner latex film provides a positive moisture barrier but, being spaced from the infant's skin by the soft and multilayered interior material, does not cause discomfort such as would occur if a nonabsorbent material were in direct skin contact.

It will be recognized that various modifications of this invention may be made without departing from the principles thereof. Such of these modifications are to be considered as included in the hereinafter appended claims unless these claims by their language expressly state otherwise.

The embodiments of the invention in which an exclusive property or privilege is claimed are defined as follows:

1. A washable, reuseable diaper, said diaper having a body; said body having a pair of ends and a pair of sides, one of said ends having a small outward curvature to give it convexity, said sides being shaped in the form of a segment of a curve extending substantially the full length of each side and convergent intermediate said ends whereby the least width of said diaper is substantially midway between the ends thereof; said body having an interior laminae, the exterior lamina having a latex inner face and a fabric exterior face; said body having an inner lamina of a multi-layered woven cotton, moisture absorbing fabric providing the only material forming the inside surface of the diaper; an elastic band secured to said body along each side intermediate said laminae, said band being spaced inwardly from the side edge of the diaper; the ends of said bands being spaced from the ends of said body; a third elastic band secured to said body along the other of said ends intermediate said laminae and spaced inwardly from the adjacent edge of the diaper; said other end when said diaper is released, having a shallow concave shape; the ends of said third band being spaced from the sides of said body; all said elastic bands being embedded within the body of said diaper whereby no portion thereof will contact an infant wearing the diaper, said elastic bands at said sides providing means for adjusting the diaper to fit closely about an infant's legs and the elastic band at the one end providing automatic means of adjusting to the waist of an infant the length of the combined ends of the diaper; detachable fastening means secured to said body at each of its four end corners and at each corner being spaced from the adjacent end of said elastic bands.

* * * * *